(12) United States Patent  
Drochner et al.

(10) Patent No.: US 8,409,283 B2
(45) Date of Patent: Apr. 2, 2013

(54) VERTEBRAL IMPLANT END CAP

(75) Inventors: Thomas E. Drochner, Memphis, TN (US); Michael J. Merves, Memphis, TN (US); Bret M. Wilfong, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 263 days.

(21) Appl. No.: 12/845,891

(22) Filed: Jul. 29, 2010

(65) Prior Publication Data

US 2012/0029634 A1  Feb. 2, 2012

(51) Int. Cl.
*A61F 2/44* (2006.01)
*B23P 11/00* (2006.01)

(52) U.S. Cl. .................................... 623/17.11; 29/428

(58) Field of Classification Search .... 623/17.11–17.16; 606/246, 247, 280–283; 29/428

See application file for complete search history.

(56) References Cited

U.S. PATENT DOCUMENTS

| | | | | |
|---|---|---|---|---|
| 6,193,756 B1* | 2/2001 | Studer et al. | ............... | 623/17.15 |
| 7,156,874 B2* | 1/2007 | Paponneau et al. | ........ | 623/17.11 |
| 8,211,178 B2* | 7/2012 | Melkent et al. | ............ | 623/17.16 |
| 8,241,363 B2* | 8/2012 | Sommerich et al. | ....... | 623/17.16 |
| 2007/0255408 A1* | 11/2007 | Castleman et al. | ........ | 623/17.11 |
| 2011/0190890 A1* | 8/2011 | Blackwell et al. | ......... | 623/17.16 |

* cited by examiner

*Primary Examiner* — Pedro Philogene

(57) ABSTRACT

An implant and method for insertion between adjacent vertebral members. The implant comprising an implant body with a base section having a plurality of base extensions, and an end cap adapted for selective axial positioning at a selected point on the base section and subsequent rotational adjustment about an implant axis. The end cap also comprising a fixed aperture and a variable aperture, both configured to receive and lockingly engage corresponding base extensions to securely maintain the end cap positioned on the base section. The fixed and variable passages are configured and located to permit rotational end cap adjustment. The implant imparts end cap height and angulation to an adjacent vertebral body at the selected or desired point when the implant is positioned and lockingly engaged in the intervertebral space.

18 Claims, 5 Drawing Sheets

VERTEBRAL IMPLANT END CAP

BACKGROUND

The present application is directed to implants, devices and methods for stabilizing vertebral members, and more particularly, to intervertebral implants, devices and methods of use in replacing an intervertebral disc, a vertebral member, or a combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions and ailments may lead to damage of the spine, intervertebral discs and/or the vertebral members. The damage may result from a variety of causes including, but not limited to, events such as trauma, a degenerative condition, a tumor, or infection. Damage to the intervertebral discs and vertebral members can lead to pain, neurological deficit, and/or loss of motion of the spinal elements.

Various procedures include replacing a section of or the entire vertebral member, a section of or the entire intervertebral disc, or both. One or more replacement implants may be inserted to replace the damaged vertebral members and/or discs. The implants are configured to be inserted into the intervertebral space and contact against adjacent vertebral members. The implants are intended to reduce or eliminate the pain and neurological deficit, and increase the range of motion.

The curvature of the spine and general shapes of the vertebral members may make it difficult for the implants to adequately contact the adjacent vertebral members or to position the adjacent vertebral members in a desired orientation. There is a need for implants or devices configurable to match the spinal anatomy for secure contact and/or desired orientation for secure contact when implanted into an intervertebral space.

SUMMARY

The present application discloses implants or devices for insertion into an intervertebral space between a first and second vertebral member, the implant comprising an implant body with a base section having at least first and second base extensions, and an end cap adapted for selective axial positioning at a selected point on the base section via rotational adjustment of the end cap about an implant axis. The end cap comprises an exterior contact surface facing away from the implant body and a seating surface adapted to contact the base section when the end cap is positioned on the base section. The end cap also comprises a fixed aperture adapted to receive a corresponding first base extension, and a variable aperture adapted to receive a corresponding second base extension, wherein the fixed aperture and variable aperture are configured to lockingly engage corresponding first and second base extensions to securely maintain the end cap positioned on the base section. The fixed and variable passages are configured and located to permit rotational end cap adjustment such that end cap height and end cap angulation can be positioned at a desired or selected point relative to the adjacent vertebral member when the implant is lockingly engaged in the intervertebral space. The implant imparts end cap height and angulation to an adjacent vertebral body at the selected or desired point when the implant is positioned in the intervertebral space.

The present application also discloses an end cap for use with an implant having an implant body with at least one base section having a plurality of base extensions. The end cap comprising an exterior contact surface, a seating surface, and an exterior cap wall extending between the exterior contact surface and the seating surface. The end cap also comprises a fixed aperture extending between the exterior contact surface and the seating surface and a variable aperture extending between the exterior contact surface and the seating surface, both adapted to receive corresponding first and second base extensions. The fixed and variable apertures enable the end cap to be axially positioned at a selected point on the implant base section. The fixed aperture and variable aperture are configured to complementarily engage corresponding first and second base extensions to securely maintain the end cap positioned on the base section. The end cap once positioned on the implant will impart an end cap angulation to an adjacent vertebral body at the selected point when the implant is axially placed and rotationally positioned in an intervertebral space.

There is also provided a method of assembling an implant for insertion into an intervertebral space between a first and second vertebral member. The method comprising positioning an end cap at an end of an implant body, where the end cap has a fixed aperture adapted to receive a corresponding first base extension that extends from the implant body and a variable aperture adapted to receive a corresponding second base extension that extends from the implant body; axially inserting the first and second base extensions into a corresponding end cap fixed aperture and variable aperture; rotating the end cap relative to the implant body to thereby simultaneously move the first and second base extensions within corresponding fixed and variable apertures; and securing the first and second base extensions within the corresponding fixed and variable apertures to thereby position the end cap to the implant body in a locked position.

The various aspects of the various embodiments may be used alone or in any combination, as is desired.

DETAILED DESCRIPTION

Figure 1:
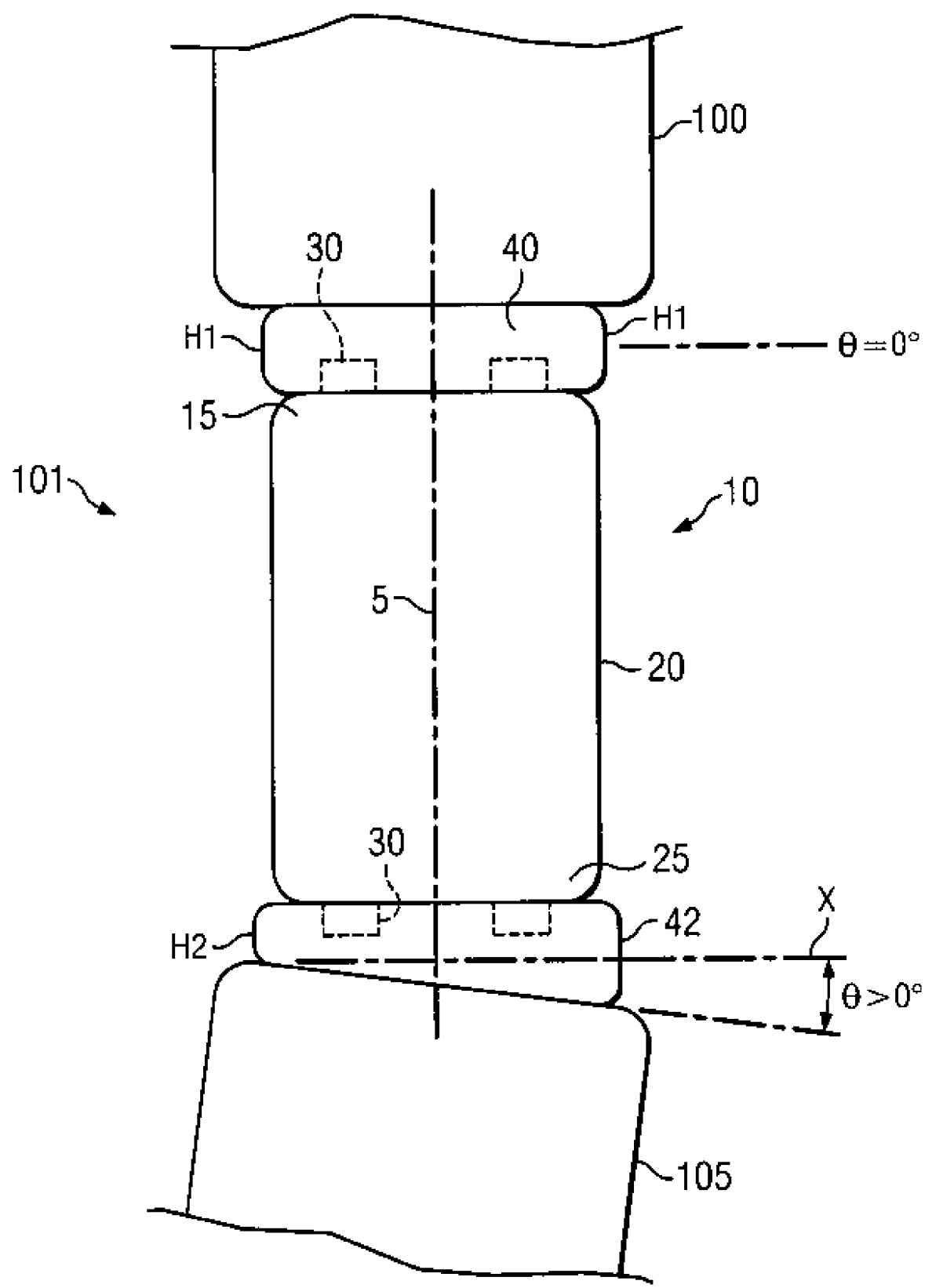
FIG. 1 is a schematic diagram of an implant according to one embodiment positioned in an intervertebral space between vertebral members.

The present application is directed to intervertebral implants for spacing apart vertebral members 100 and 105. FIG. 1 shows an implant 10 positioned within an intervertebral space 101 formed between vertebral members 100 and 105. The implant 10 includes an implant body 20 and one or more end caps 40 and 42 which are attached to the implant body 20 at a first or second implant base section 15 and 25 via base teeth or base extensions 30. The end caps can be an upper end cap 40 or a lower end cap 42. The one or more end caps 40 and 42 will attach or connect to the implant body 20 to impart a desired or selected angulation θ, an angular orientation and/or an end cap position to the adjacent vertebral member 100 or 105. A first and second securing or locking mechanism 50 and 60, shown in one aspect in FIGS. 2, 4 and 5 engages and locks the end cap 40 and 42 to the implant base section 15 and 25. This will improve the contact and stability of the intervertebral implant 10 to the adjacent vertebral members 100 and 105 and drive angular orientation and position for correction and/or improved alignment of the spine.

As shown in FIG. 1, the implant 10 may include first and second end caps 40 and 42 positioned at opposite ends of the implant body 20 at first and second base sections 15 and 25. The first end cap may be an upper end cap 40 and the second end cap may be a lower end cap 42. A first end cap 40 can have an angulation θ of zero degrees and a first end cap height H1, as shown in FIGS. 1-3 and 5. The second end cap 42 can have an angulation θ greater than zero degrees, for example of 15° degrees, and a second height H2. Those of skill in the art will recognize that the first and second end caps 40 or 42 may have the same or different configuration, heights H, and/or the same or different end cap angulation θ. Further, although two end caps 40 and 42 are shown in the disclosed aspects, those of skill in the art will recognize that one or two end caps 40 or 42 may instead be used in a medical procedure with the implant 10, and that the end caps can be attached to either the first and second base sections 15 and 25, to impart desired or needed heights H and angulation θ to adjacent vertebral members 100 or 105 to thereby correct, improve and/or stabilize the affected spinal anatomy.

Figure 2:
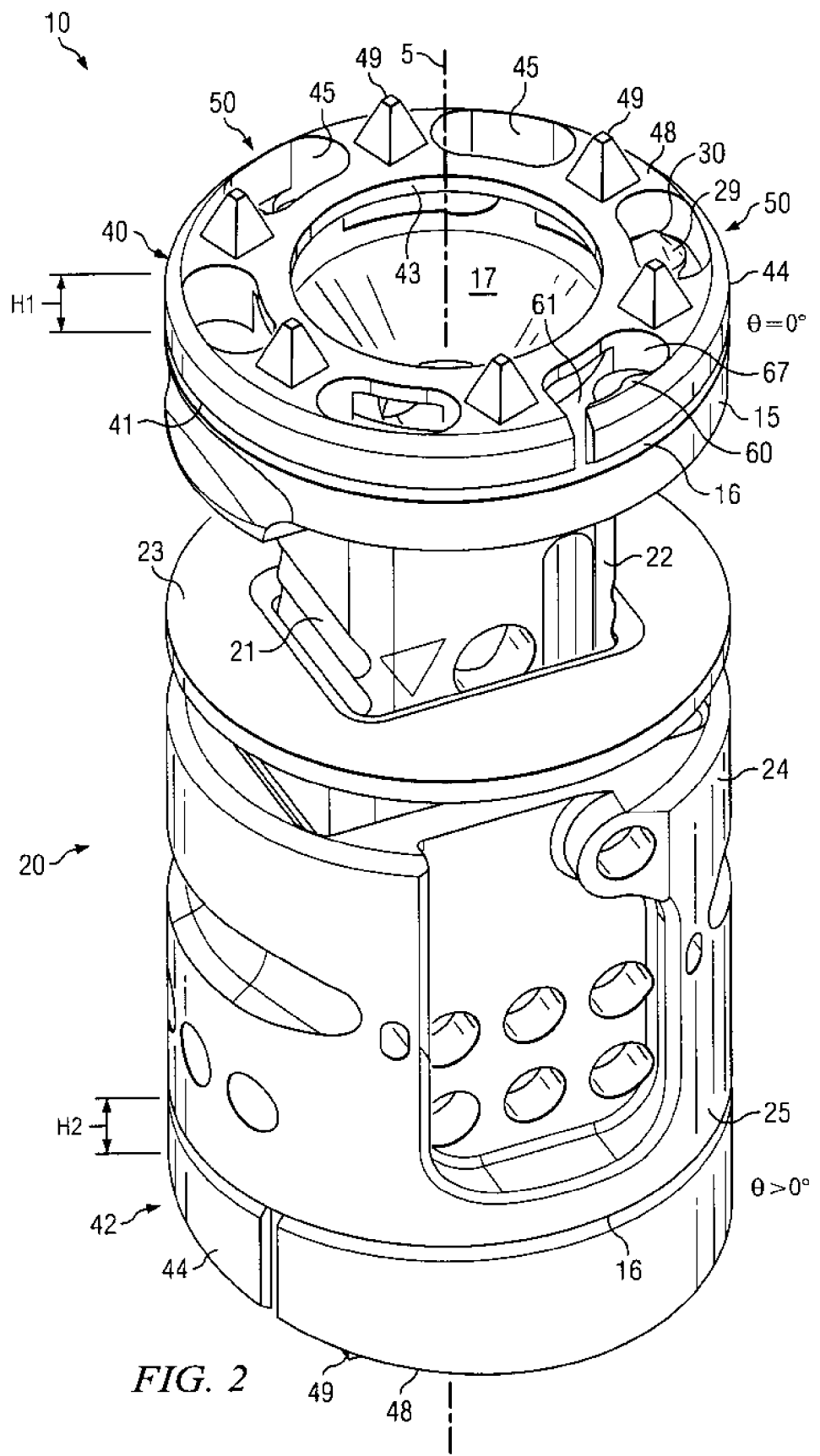
FIG. 2 is a perspective view of an implant with an end cap attached thereon according to one embodiment.
Figure 3:
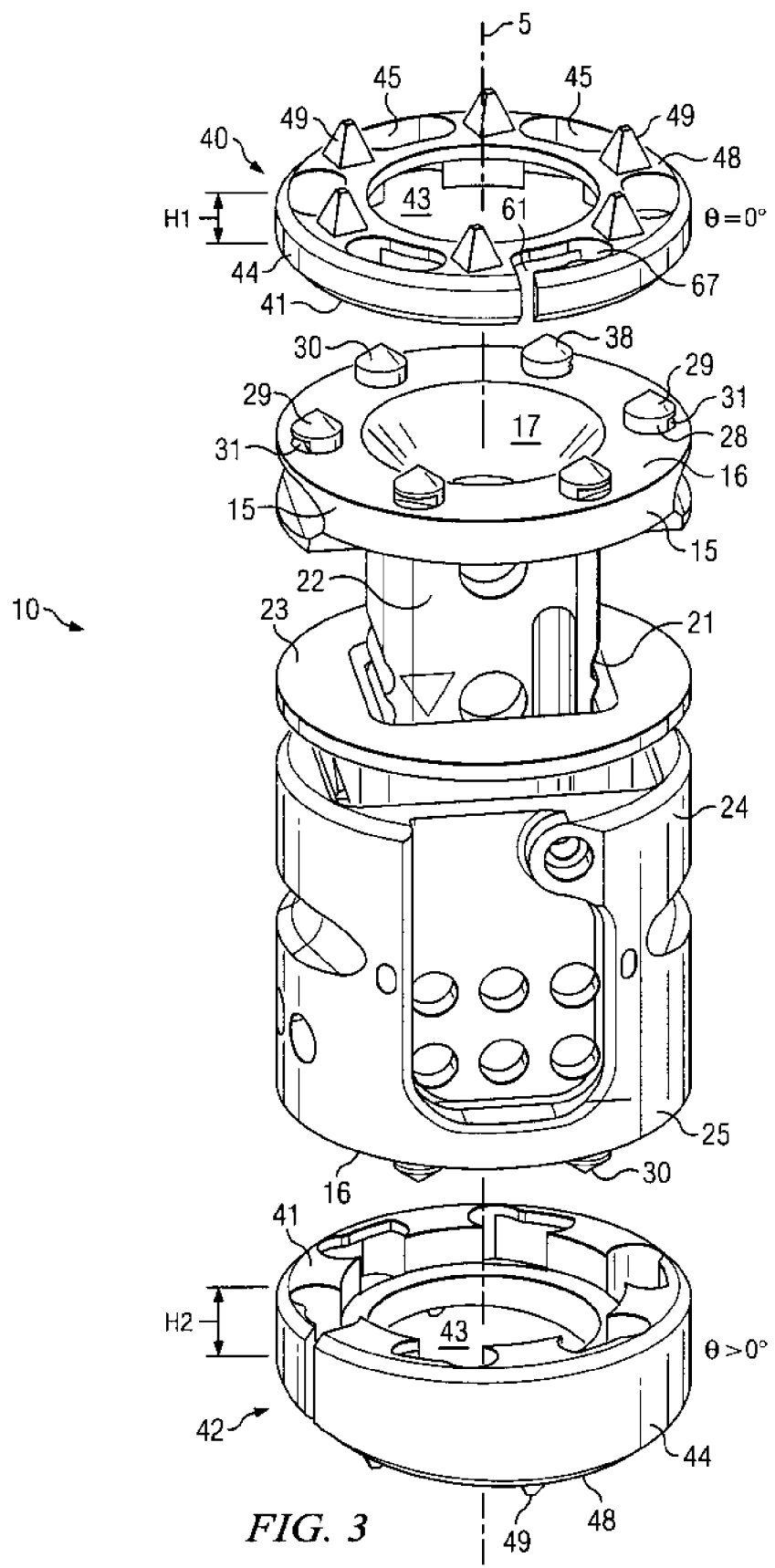
FIG. 3 is an exploded perspective view of the implant and end cap of FIG. 2.
Figure 4:
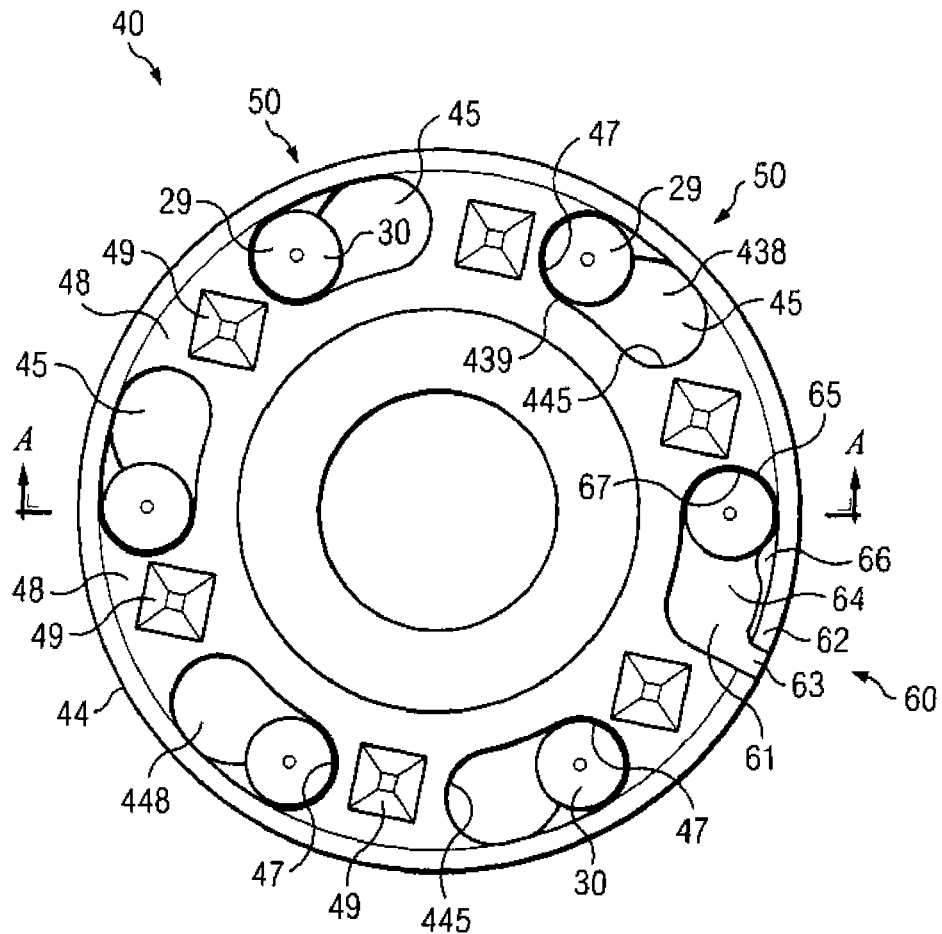
FIG. 4 is a top view of the implant and an end cap of FIG. 2.
Figure 5:
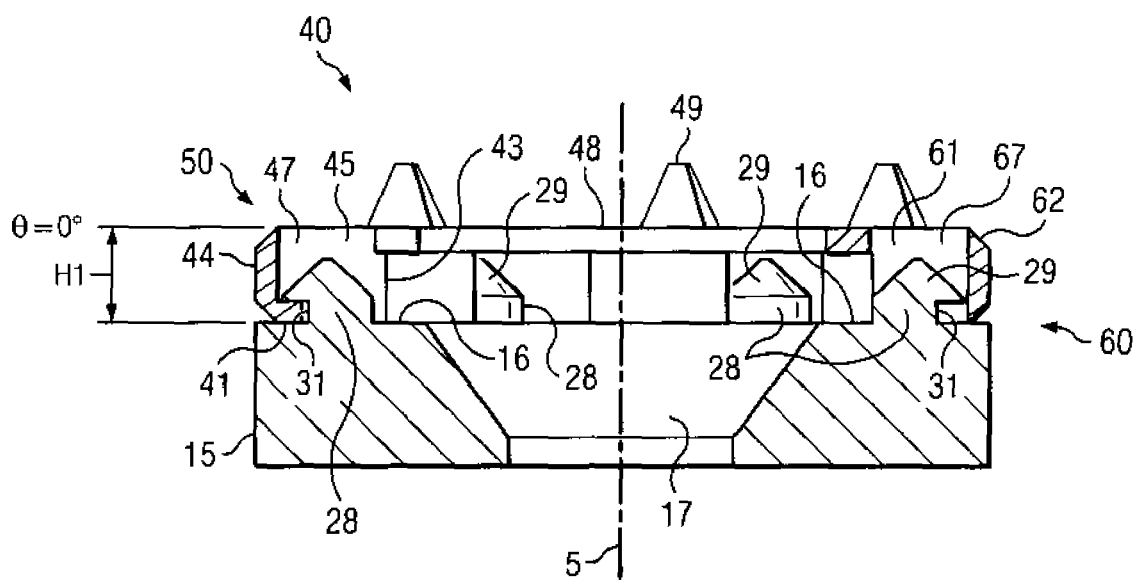
FIG. 5 is a section view along the line A-A of the implant and end cap of FIG. 4.

FIGS. 2-3 illustrate assembled and exploded perspective views of an implant 10 with upper and lower end caps 40 and 42 according to one embodiment. FIG. 4 is a top view of the assembled implant 10 and an end caps 40 and 42 of FIG. 2. FIG. 5 is section view along the line A-A of the assembled implant 10 and an end caps 40 and 42 shown in FIG. 2 showing in more detail securing or locking mechanism a with a first securing feature 50 and second securing feature 60. The implant body 20 in combination with the end caps 40 and 42 is sized to fit within the intervertebral space 101. In this aspect, the implant body 20 is constructed of two implant sections 22 and 24 which are movable relative to each other to permit axial adjustment of the overall axial height of the implant 10. The implant body 20 includes an inner implant body 22 adapted to axially travel inside an outer implant body 24 to thereby enable selected or controlled collapse and expansion of the implant 10. The outer implant body 24 includes a hollow interior and the inner implant body 22 includes a first base section 15. The inner implant body 22 is sized to fit within and axially travel along the hollow interior of the outer implant body 24 to adjust the height of the implant body 20 along the longitudinal axis 5. The inner body 22 includes a neck area with a plurality of scallops 21 that extend along the length of the inner body 22. Both the inner and outer implant bodies 22 and 24 may be hollow and include one or more apertures to receive bone growth material. Also, one or more apertures may extend through the body 20 walls to the hollow interior. The implant body 20 may also be constructed from a single section with a fixed height measured between the first and second base sections 15 and 25.

A securing mechanism 23 may secure the inner and outer sections 22 and 24 together to fix the height. In one embodiment, the securing mechanism 23 is configured to receive one or more cylindrical rods (not illustrated) that seat within the plurality of scallops 21 that extend along the inner body 22 neck. U.S. Patent Publication No. 2008/0114467 discloses embodiments of an implant that may be used with end caps and include a multiple-section body and a locking mechanism and is herein incorporate by reference in its entirety.

FIGS. 2-5 illustrate the implant body 20 which is configured to receive an end cap 40 or 42 at the first and second base sections 15 and 25. The first and second base sections 15 and 25 have an exterior support surface or support surface 16 that extends around the periphery of a corresponding central base aperture 17. In the disclosed embodiment, the support surface 16 is substantially flat, although other embodiments may include a variety of different surface configurations. The base sections 15 and 25 include a plurality of base teeth or base extensions 30 that extend axially away or outward from the support surface 16. The base extensions 30 are preferably evenly spaced around the periphery of the base section 15 and 25 and extend away from an exterior surface 16 of the first base section 15 in a substantially outward or axial direction. The base extensions 30 are sized and configured to extend into corresponding end cap locking apertures or passages 45 or 61 when the end cap 40 or 42 is positioned onto the base section 15 and 25. The outer implant body 24 includes a second base section 25 with similarly positioned and configured base teeth 30. FIGS. 2, 3 and 4 illustrate an embodiment where the implant base sections 40 or 42 have six (6) extending base teeth or base extensions 30 that are equidistantly spaced about the support surface 16 about or around the periphery of the central base aperture 17. As such, in this embodiment, the six extending base teeth 30 are spaced at or about 60° apart from each other around the periphery of the implant base section 15 or 25. Other embodiments are contemplated which could include two or more base extensions 30 or at least two base extensions 30. For example, the locking aperture or passages 45 and 61 could be spaced or located at non-equidistant points around the end cap area between the vertical exterior cap wall 44 and the central aperture 43 as may be desired or required by a surgical procedure or clinical application, or surgeon need or selection. However, in the non-equidistant spacing or locating case, the locking apertures 45 and 61 need to be spaced and located to complementarily align with the spacing and location of the base teeth 30 to permit axial end cap 40 insertion and rotational engagement with the base teeth 30 of the implant base section 15 or 25.

The implant base section's 15 and 25 central base aperture 17, shown in FIGS. 2, 3 and 5, is adapted to receive or permit delivery of bone growth material into the implant 10 which will augment fusion in the disc space 101 once the implant is in place between the vertebral members 100 and 105. The base apertures 17 are preferably adjacent and aligned with a corresponding end cap central aperture 43. Those of skill in the art will recognize that the base aperture 17 and end cap central apertures 43 may also be non-aligned if desired or needed by a surgeon, medical procedure or clinical application.

The base teeth or base extensions 30 include a tooth base or stem 28 that extends axially outward from the support surface 16 and are capped with a tooth head 29. The tooth head 29 includes a tapered shape or configuration, for example similar to a solid cone shape, that terminates at a tip. The tooth head tip facilitates entry and travel into a corresponding end cap locking aperture or passage 45 or 61 when the end cap 40 or 42 is positioned and placed on the base section 15 and 25. The tooth head tip may also be appropriately shaped to directly contact against and/or penetrate into an adjacent vertebral member 100 or 105 when the implant 10 is used without an end cap 40, or when the base tooth or base extension 30 extends beyond the end cap 40. As best illustrated in FIGS. 3 and 5, the tooth base or stem 28 comprises a smaller width than the tooth head 29 forming an undercut tooth section or notch 31. The depth of the undercut tooth section 31 may be the same or different for each of the base teeth or base extensions 30. The undercut tooth sections 31 may face radially outward from the central base aperture 17. One or more base teeth or base extensions 30 may include a tooth base or stem 28 that have substantially the same width as the tooth head 29. In one embodiment, the width of the tooth stem 28 is equal to the widest part of the tooth head 29.

The end cap 40 or 42, via its end cap locking apertures or passages 45, can be attached to the implant body 20 via the base teeth or base extensions 30 when the end cap 40 or 42 is placed and positioned on the base section 15 and 25. The overall width or distance across the end cap 40 or 42 preferably matches the width or distance across the base section 15 and 25 such that the end cap 40 or 42 does not extend past the lateral side walls of the implant body 20. In other embodiments, the end cap 40 or 42 may have a width or distance across the end cap 40 or 42 that is greater or smaller than width or distance across the base section 15 and 25 such that the end cap 40 or 42 would extend or would not extend, respectively, past the lateral side walls of the implant body 20 depending on the desire or needed of a surgeon, medical procedure or clinical application.

FIGS. 2-4 and 6-7 illustrate that the end cap 40 comprises an annular or circular like shape with an outside or exterior contact surface 48, locking apertures or passages 45 and 61, an interior or seating surface 41, a substantially vertical exterior end cap wall 44 and a central aperture 43. The end cap 40 may take on a variety of geometric shapes desired or needed by a surgeon, medical procedure or clinical application. Other shapes include but are not limited to polygonal and crescent-shaped. The end cap 40 may also include a central aperture 43 that may also have various geometric shapes.

The exterior contact surface 48 and the seating surface 41 are bounded by the vertical exterior end cap wall 44 and the central aperture 43. The seating surface 41 is preferably substantially flat to complementarily abut against the exterior support surface 16 of the implant base section 15 or 25. In a preferred aspect, the seating surface 41 and the exterior surface 16 have complementary and substantially flat surfaces such that the end cap 40 can seat flush on the implant base section 15. The exterior contact surface 48 extends around the central aperture 43. The exterior contact surface 48 may also be flat, or may include various other configurations to facilitate contact with the vertebral member 100 or 105. Those of skill in the art will recognize that the seating surface 41 and exterior contact surface 48 may take on other configurations as may be desired or needed by a surgeon, medical procedure or clinical application. The central aperture 43 is preferably aligned with and the same size as the corresponding base aperture 17. The central aperture 43 and base aperture 17 may also be of different sizes and non-aligned if desired or needed by a surgeon, medical procedure or clinical application.

The exterior contact surface 48 includes end cap teeth 49 which will engage the end plates of an adjacent vertebral member 100 or 105 to assist the implant 10 grip the vertebral member end plate, provide implant 10 stability in the disc space 101, and prevent implant 10 ejection from the intervertebral space 101. The end cap teeth or spikes 49 may be a series of equidistantly spaced end cap teeth or spikes 49 extending from the end cap exterior surface 48, as shown in FIGS. 2-7. Those of skill in the art will recognize that the number, size, shape, orientation and spacing of the end cap teeth 49 may vary according to the needs of a medical procedure, clinical application, or surgeon need or selection. For example, the end cap teeth or spikes 49 could also be a series or pattern of uniform knurls and spikes 49 (not shown) that cover the end cap exterior surface 48 and assist in providing a securing and stabilizing function of the combined end cap 40 or 42 and implant body 20 or solely a series or pattern of uniform knurls (not shown) that cover the end cap exterior surface 48, so long as they assist in providing a securing and stabilizing function of the combined end cap 40 or 42 and implant body 20. Those of skill in the art will recognize that the number, size, height, shape, orientation and spacing of the end cap teeth or spikes 49 may vary according to the needs of a medical procedure or clinical application.

The end cap teeth 49 may contact the adjacent vertebral member 100 or 105 and/or penetrate into the vertebral member 100 or 105 as may be desired or required by a physician or medical procedure or clinical application. In one aspect, the end cap teeth or spikes 49 will come in contact with and engage the end plates of an adjacent vertebral body 100 or 105 once the combined implant body 10 and end cap 40 or 42 are positioned in an intervertebral space 101 between the vertebral members 100 and 105. The end cap teeth or spikes 49 will extend from the end cap exterior surface 48 sufficiently to grip, penetrate and embed into the adjacent vertebral member 100 and 105 end plate to thereby provide implant stability in the intervertebral disc space 101 and prevent the inserted implant 10 from being ejected out of the intervertebral space 101 after implant 10 insertion. The end cap teeth or spikes 49 will provide a securing and stabilizing function of the combined end cap 40 and implant body 10. The actual height of the end cap teeth or spikes 49 can vary to accommodate the selection or need of a surgeon, medical procedure or clinical application. When an implant 10, with positioning base teeth 30 and one or two end caps 40 or 42, is inserted into an intervertebral space 101 and set to a desired implant height, via appropriate instruments (not shown), the protruding end cap teeth or spikes 49 will grip and/or penetrate into the adjacent vertebral member end plate to maintain a stable implant 10 position between the adjacent vertebral members 100 and 105.

The end cap 40 or 42 preferably further comprises an angulation aspect $\theta$ and an end cap vertex height H. The end cap angulation $\theta$ and cap height H may have a range of values as may be selected or needed by a surgeon, medical procedure or clinical application. In one aspect, preferred discrete values for end cap angulation are 0°, 4°, 8° and 15° degrees measured from an angulation reference line X, shown in FIG. 1. In other embodiments, the preferred angulation $\theta$ values may be in the range of zero and thirty degrees (0°-30°), with a preferred range of between zero and fifteen degrees (0°-15°). In one aspect, the cap height H may have preferred values in 1.0 mm or 0.5 mm increments measured from the end cap seating surface 41. The angulation reference line X is preferably at the cap height H value as shown in FIG. 1. The end cap's angulation $\theta$ is a measure of the inclination of the exterior contact surface 48 relative to the angulation reference line X. Insertion of an implant 10 with an end cap 40 or 42 having an angulation $\theta$ aspect enables the end cap 40 or 42 to impart a desired or selected angulation $\theta$ to an adjacent vertebral member 100 or 105. In this manner, selective angulation $\theta$ can be imparted to the adjacent vertebral body 100 or 105 and thereby assist in the correction and/or improved orientation, stabilization and alignment of the spine. In the event where additional implant height H is desired or required without any angulation, an end cap 40 having angulation θ of 0° degrees may be used to impart the additional height to the implant 10 in the amount of an end cap height H. Such a case is illustrated in FIGS. 2-3 and 5-6 which show views of an implant base section 15 with an end cap 40 having angulation θ of 0° degrees and a certain cap height H. Additionally, selected angulation θ may advantageously and appropriately accommodate the lordotic or kyphotic shape of the spine depending upon the vertebral level at which the implant 10 is to be positioned in the patient.

FIGS. 1-3 show a first or upper end cap 40 and a second or lower end cap 42. The first and second end caps 40 or 42 may have the same or different configuration, heights H, and/or the same or different end cap angulation θ. As shown in FIGS. 1-3, the upper end cap 40 has an angulation θ of zero degrees and a first end cap height H1. FIGS. 1-2 show that the lower end cap 42 has an angulation θ greater than zero degrees (0°) and a second height H2. As noted previously, values for an end cap angulation can be 0°, 4°, 8° and 15° degrees measured from an angulation reference line X, or values in a range of zero and thirty degrees (0°-30°), with a preferred range of between zero and fifteen degrees (0°-15°). Those of skill in the art will recognize that end caps 40 or 42 with the same or different end cap angulation θ and the same or different end cap heights H1 or H2 may instead be used. Although two end caps 40 and 42 are shown in the disclosed aspects, those of skill in the art will also recognize that one end cap may instead be used, either as a lower or upper end cap, in a medical procedure with the implant 10 to impart desired or needed height H and angulation θ to adjacent vertebral members 100 or 105 and thereby correct, improve and/or stabilize the affected spinal anatomy.

FIGS. 1-3 show an aspect where the upper end cap 40 provides an angulation θ of zero degrees (0°) and is attached to the inner implant body 22 at the upper implant base section 15. In this aspect, the upper end cap 40 provides an end cap height H1 but will not provide any implant angulation θ. Such an end cap 40 may be used where there is a need only for additional height to augment the implant 10 in the amount of an end cap height H1 as might be desired or required by a surgeon, medical procedure or clinical application. FIGS. 1-3 also show an aspect where the lower end cap 42 provides an angulation θ greater than zero degrees (θ>0°) and attached to the outer implant body 24 at the lower implant base section 25. In this aspect, the lower end cap 42 provides an end cap height H2 and an implant angulation θ>0°. Such an end cap 42 may be used where there is a need for both additional height to augment the implant 10 in the amount of end cap height H2 and end cap angulation θ greater than zero degrees (θ>0°) as might be desired or required by a surgeon, medical procedure or clinical application.

FIGS. 2-4 and 6-7 show an end cap 40 or 42 which includes one or more locking apertures or passages 45 or 61 that receive corresponding base teeth 30 extending from the implant body 20 base sections 15 or 25. The locking apertures 45 or 61 are spaced around the end cap 40 or 42 to complementarily correspond to and accommodate the positioning of the base teeth or base extensions 30 extending from the base sections 15 or 25 when the end cap 40 or 42 is axially placed and then positioned on the implant body 20. In one aspect, shown in FIGS. 2-4, the fixed or closed apertures 45 comprise a continuous sidewall 445. The apertures 45 include a wide section 438 and a narrow section 439. The wide section 438 includes a greater width measured between opposing surfaces than the narrow section 439. The wide section 438 is wider than the base tooth head 29 of the base extension 30 to allow the end cap 40 or 42 to be axially mounted onto the implant body 20. The narrow section 439 is narrower than the base tooth head 29 which thereby permits the end cap 40 or 42 to be rotationally positioned and secured to the implant body 20.

An aperture protrusion or projection 431 extends into the aperture 45 from the sidewall 445 to form the edge of the narrow section 439. The aperture protrusion 431 is configured to fit within the undercut section 31 below the tooth head 29 of the base tooth or base extension 30 to attach and secure the end cap 40 or 42 to the implant body 20. The aperture protrusion 431 is located or recessed below the end cap exterior surface 48. This recessed positioning locates the aperture protrusion 431 such that it can fit under the tooth head 29 of the base tooth or base extension 30 and within the undercut section 31 when the end cap 40 or 42 is attached, positioned and secured to the implant body 20, as best shown in FIG. 5.

When the end cap 40 or 42 is axially positioned on the base section 15 or 25, the base extensions 30 will enter into a corresponding wide sections 438 of the one or more end cap apertures 45. Once the end cap 40 or 42 is axially seated on the exterior surface 16 of the implant base section 15 or 25, the base extensions 30 are located in the wide section 438 of a corresponding fixed aperture 45. The end cap 40 or 42 and/or the implant base section 15 or 25 can then be appropriately rotated, in one aspect disclosed in a clockwise direction, so that the aperture protrusion 431 will travel until the aperture protrusion 431 is in complementary and mechanical communication with the undercut section 31 of the base tooth or base extension 30 in the narrow section 439 of the and cap aperture 45, as shown in FIGS. 2, 4 and 5. Once the end cap 40 or 42 is in the narrow section 439 of the fixed aperture 45, if the positioning teeth 30 continue to travel in the aperture 45, the positioning teeth 30 will reach and abut up against a narrow section stop wall 47 located opposite the wide section 438 of the aperture 45. When the base teeth 30 reach and abut up against the aperture stop wall 47, the aperture stop wall 47 will obstruct and prevent further travel of the positioning teeth 30 inside the aperture 45. If an attempt is made to continue to rotationally move or force the end cap 40 or 42 to travel on the implant base section 15 or 25, the aperture stop wall 47 will prevent further travel of the positioning tooth 30. The end cap 40 or 42 has reached a secured or locked position, shown in FIGS. 2 and 4, on the implant body base section 15 or 25. At this point, as shown in FIG. 5, the aperture protrusion 431 is in complementary and mechanical communication with the undercut section 31 of the base tooth or base extension 30 below the tooth head 29. The mechanical communication between the aperture protrusion 431, the undercut section 31, the teeth heads 29 and aperture stop walls 47 can comprise a first securing or locking mechanism 50.

In the secured or locked position, the end cap 40 or 42 is in an engaged or locked position relative to the implant body 20. The aperture protrusion 431 and the undercut section 31 are preferably and complementarily sized such that, at the engaged and locked position, e.g., as shown in FIGS. 2, 4 and 5, the fit between the aperture protrusion 431 and the undercut section 31, and by extension the positioning teeth 30 and fixed apertures 45 is a friction fit. The friction fit should permit the positioning teeth 30 to travel inside the narrow sections 439 so that the aperture protrusion 431 and the undercut section 31 can reach an engaged or locked position when the end cap 40 or 42 is moved relative to the first or second base section 15 or 25 towards the aperture stop walls 47. The friction fit, when the aperture protrusion 431 and the undercut section 31 are in mechanical communication should be sufficiently strong to minimize or significantly retard rotational movement between the positioning teeth 30 and end cap fixed apertures 45 once the end cap 40 or 42 is positioned in the engaged or locked position cap position on the first or second base section 15 or 25.

The friction locking aspect can form part of the first securing locking mechanism 50. The holding strength of the friction fit between the positioning teeth 30 and end cap apertures 45, via the aperture protrusion 431 and the undercut section 31, may be augmented or controlled by the addition or use of a coating or adhesive substance between the aperture protrusion 431 and the undercut section 31. For example, a coating, such a silicone, or an adhesives such as an epoxy, may be used to increase friction between the aperture protrusion 431 and the undercut section 31. Those of skill in the art will recognize that other substances or friction control mechanisms may be used to augment or control friction strength between the end cap slots 45 and the positioning teeth 30, such as roughened surfaces, dissimilar materials, and shape differences.

The complementary and mechanical communication between the aperture protrusion 431 and the undercut section 31 will prevent axial movement or travel of the end cap 40 or 42 away from the implant base section 15 or 25 along the implant axis 5. This is the case since the aperture protrusion 431 is now positioned underneath and obstructed by the base extension head 29. An attempt to axially move or remove the end cap 40 or 42 away from the implant base section would result in the aperture protrusions 431 bumping into and abutting the underside of the teeth heads in the undercut sections 31. The teeth heads 29 thus prevent axial movement of the end cap 40 or 42 away from the implant base section 15 or 25 along the implant axis 5 once the end cap 40 or 42 is in a secured or locked position with the base section 15 or 25. The number of apertures 45 in an end cap 40 or 42 may vary from a single to multiple apertures 45. FIGS. 2-7 illustrate an embodiment with five (5) axially attaching and rotationally positioning fixed or closed apertures 45.

FIGS. 2-7 show that the end cap 40 or 42 further includes a variable aperture 61 that is adapted to receive a corresponding base tooth or base extension 30 extending from the implant body 20 base sections 15 or 25. The variable aperture 61 will simultaneously act in combination with the one or more end cap fixed apertures 45 to enable the end cap 40 or 42 to be axially attached, positioned and secured to the implant body 20 when the end cap 40 or 42 is axially placed and rotationally positioned on the base teeth 30 of the implant body base sections 15 or 25. FIGS. 2-7 show an embodiment with a single variable aperture 61 adapted to receive a corresponding base tooth or base extension 30 extending from the implant body 20 base sections 15 or 25 when the end cap 40 or 42 is axially attached on the implant body 20. However, the end cap 40 or 42 may have one or more variable apertures 61. FIGS. 2-7 show an embodiment of an end cap 40 or 42 with five fixed apertures 45 and one variable aperture 61. For example, in another aspect, the end cap 40 or 42 could instead have four fixed apertures 45 and two variable apertures 61. Those of skill in the art will recognize that an end cap 40 or 42 could have a varying combination of fixed and variable apertures 45 and 61 where there are the same or a different number of fixed apertures 45 and variable apertures 61 as might be desired or needed by a surgeon, medical procedure or clinical application. Further, the fixed apertures 45 and variable aperture 61 may have the same or different shape, configuration and/or sizes.

Figure 6:
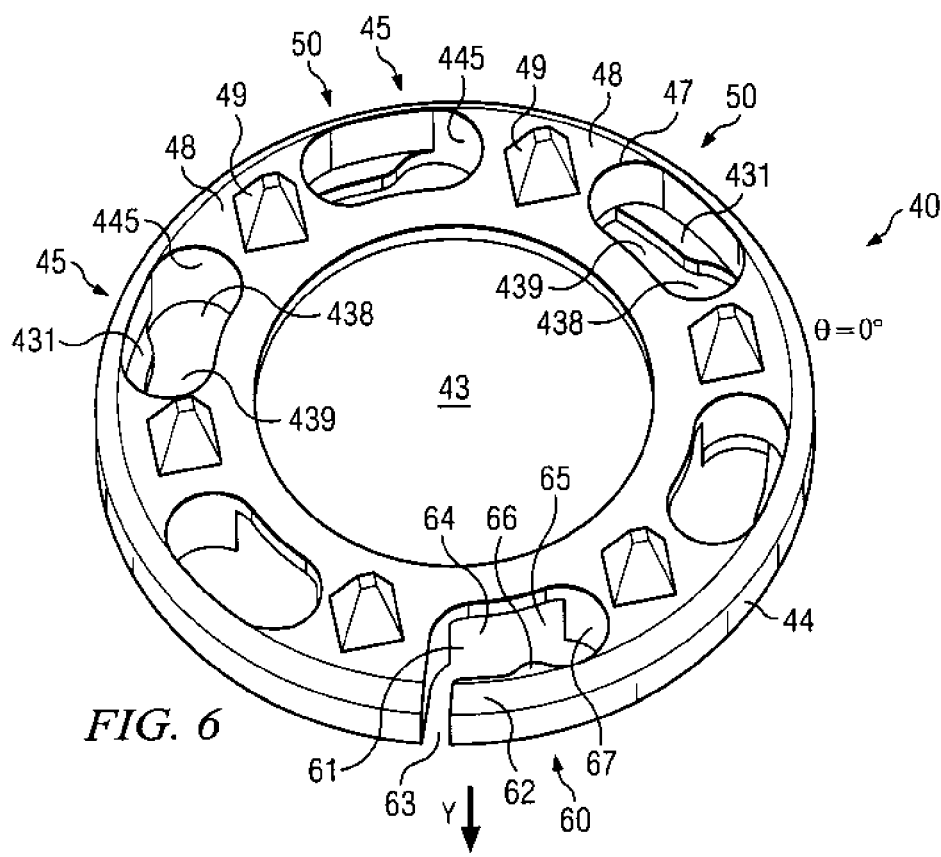
FIG. 6 is a perspective view of an implant end cap according to one embodiment.
Figure 7:
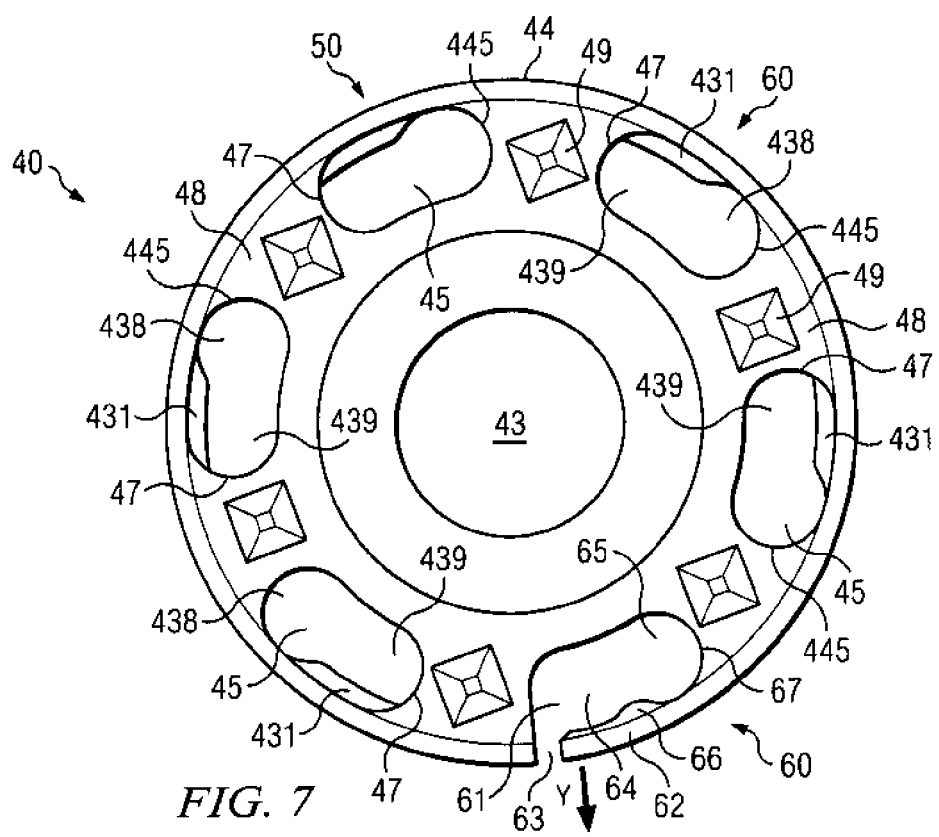
FIG. 7 is a top view of the end cap of FIG. 6.

As best shown in FIGS. 6-7, the variable aperture 61 preferably comprises an aperture finger 62, a slot 63, a first interior space 64, a second interior space 65 and a variable aperture stop wall 67 opposite the slot 63. The slot 63 extends between the first interior space 64 and the exterior edge of the end cap wall 44. The slot 63, first interior space 64 and second interior space 65 are in spatial orientation with each other so that the flexible aperture finger 62 is formed in an exterior portion of the variable aperture 61 along a portion of the end cap's 40 or 42 exterior end cap wall 44. Additionally, the aperture finger 62 comprises an aperture finger projection or protrusion 66 which extends inward between the first interior space 64 and second interior space 65. The first interior space 64 is wider than the base tooth head 29 of the base extension 30 to allow the end cap 40 or 42 to be axially mounted onto the implant body 20. The second interior space 65 is preferably sized to, in combination with the flexible finger protrusion 66, accommodate the base tooth head 29 when the end cap 40 or 42 is rotated into a locked position and secured to implant body 20, as best shown in FIG. 4. In the disclosed embodiment, the aperture finger projection or protrusion 66 preferably extends the height of the exterior end cap wall 44. In other aspects, the finger projection or protrusion 66 may have a height that is less than the exterior end cap wall 44.

FIGS. 2-7 show an embodiment with a single variable aperture 61 having a corresponding single aperture finger 62 adapted to receive and engage a corresponding base tooth 30 extending from the implant body 20 base sections 15 or 25 when the end cap 40 or 42 is axially attached and rotationally secured on the implant body 20. The end cap 40 or 42 may, in other aspects, have more than one variable aperture 61 which in turn leads to having more than one corresponding aperture finger 62. FIGS. 2-7 show an embodiment of an end cap 40 or 42 with five fixed apertures 45 and one variable aperture 61 with its single corresponding aperture finger 62. In another aspect, for example, the end cap 40 or 42 could have four fixed apertures 45 and two variable apertures 61 with two corresponding aperture fingers 62. Those of skill in the art will recognize that an end cap 40 or 42 could have a varying combination of fixed and variable apertures 45 & 61 and corresponding aperture fingers 62 where there are the same or a different number of fixed apertures 45, variable apertures 61 and aperture fingers 62 as might be desired or needed by a surgeon, medical procedure or clinical application.

The material or composition make up of the end cap 40 or 42, and the relative position and configurations of the variable aperture 61, slot 63 and first and second interior space 64 and 65 result in an aperture finger 62 which has physical characteristics and properties whereby the aperture finger 62 is flexible and moveable. In this manner, the aperture finger 62 can move, flex or deflect from an original equilibrium or static position if a deflecting force is encountered by the aperture finger 62. When the aperture finger 62 encounters a deflecting force sufficient to overcome its stationary or static position and/or relative inertia, the aperture finger 62 will move or deflect in an outwardly direction Y depicted in FIGS. 6-7. This flexibility enables the aperture finger 62 to move or deflect outwardly to thereby enlarge the size of the variable aperture 61 in order to permit the base tooth 30 or tooth head 29 to travel in the variable aperture 61 towards a locked position, shown in FIGS. 2 and 4 when the end cap 40 or 42 is axially attached and rotationally positioned on the implant body 20 base section 15 or 25.

The variable aperture finger 62, aperture finger protrusion 66 and rear aperture wall 67 will interact and cooperate with a corresponding positioning tooth 30 when the end cap 40 or 42 is axially placed or attached and rotationally positioned in the implant base section 15 or 25. The variable aperture passage 61 is sized to permit a positioning tooth 30 to axially enter and slideably travel within the variable aperture passage 61 as the end cap 40 or 42 is axially placed on the base section 15 or 25 and then rotationally positioned or rotated on the base sections 15 or 25. The complementary positioning tooth 30, variable aperture 61, the variable aperture finger 62, aperture finger protrusion 66 and rear aperture wall 67 enable the end cap 40 or 42 to be axially attached and rotationally positioned onto the base section 15 or 25 to thereby form a second locking feature or end cap locking mechanism 60, shown in FIGS. 2, 4 and 5, which permits the end cap 40 or 42 to be set into a secured or locked position.

When the end cap 40 or 42 is axially moved downward and placed on the implant body 20 base section 15 or 25, a corresponding base tooth 30 will enter into the first interior space 64 of the variable aperture 61. When the end cap 40 or 42 is axially seated on the exterior surface 16 of the implant base section 15 or 25, the base extension 30 is located in the first interior space 64 of the variable aperture 61 and the aperture finger 62 is contacting the edge of the tooth head 29. At the same time, as described previously, base extensions 30 have also entered into and are now positioned in corresponding wide sections 438 of the one or more end cap fixed apertures 45.

In order to reach the an end cap engaged or locking position, as shown in FIGS. 2, 4 and 5, the end cap 40 or 42 is then rotated relative to the base section 15 or 25, so that the base teeth or base extension 30 will travel inside the variable aperture passage 61 substantially from a position at or near the aperture passage slot 63 in the first interior space 64 towards the aperture finger protrusion 66 and the variable aperture stop wall 67 in the second interior space 65. In the disclosed embodiment, the end cap 40 or 42 is rotated in a clockwise direction. As the end cap 40 or 42 is rotated and travels towards the engaged or locking position, the positioning tooth 30 travels inside the aperture interior space 64 towards the aperture finger protrusion 66. As the positioning tooth 30 continues to travel inside the first interior space 64, the positioning tooth 30 encounters and abuts the aperture finger protrusion 66 which extends interiorly into the variable aperture 61 from the aperture finger 62. As the rotational positioning movement continues, a force is imparted by the tooth head 29 against the aperture finger 62.

As the positioning tooth 30 continues to travel in the variable aperture 61 due to the end cap's 40 or 42 forced rotation the force imparted by the tooth head 29 increases. The base tooth 30 will impart a deflecting force on the aperture finger protrusion 66 and by extension the aperture finger 62. When the deflecting force attains a strength sufficient to overcome the aperture finger's 62 equilibrium or static position, the aperture finger 62 will begin to flex or deflect outward from its static position in the direction of arrow Y as illustrated in FIGS. 6 & 7. The aperture finger 62 will continue to flex or deflect so long as the deflecting force from the end cap 40 or 42 rotational positioning continues.

As the aperture finger 62 deflects outwardly, the aperture finger protrusion 66 also correspondingly deflects outwardly to permit the positioning tooth 30 to continue to travel further inside variable aperture 61 from the first interior space 64 towards the variable aperture stop wall 67 in the second interior space 65. When the positioning tooth 30 travels past the aperture finger protrusion 66, the outward deflecting force being imparted by the positioning tooth 30 to the aperture finger protrusion 66 is removed. With the outward force on the aperture finger protrusion 66 removed, the aperture finger's 62 resilient or spring-like properties will force or bias the aperture finger 62 back in an inward direction, opposite of the arrow Y.

Once the positioning tooth 30 travels past the aperture finger protrusion 66, as shown in FIG. 4, the positioning tooth 30 reaches and abuts up against the variable aperture stop wall 67 located in the second interior space 65 opposite the aperture slot 63. When the base tooth 30 reaches and abuts up against the variable aperture stop wall 67, the variable aperture stop wall 67 will obstruct and prevent further travel of the positioning tooth 30 inside the second interior space 65. If an attempt is made to continue to move or force the end cap 40 or 42 to rotationally travel on the implant base section 15 or 25, the variable aperture stop wall 67, in combination with the fixed aperture stop walls 47 of the other end cap fixed apertures 45, will prevent further travel of the positioning teeth 30. When at least one positioning or base tooth 30 reaches and abuts against a corresponding stop wall 47 or 67, the end cap 40 or 42 has reached the secured or locked position, shown in FIGS. 2 and 4, on the implant body base section 15 or 25. At this point, the end cap 40 or 42 is attached and secured to the implant body 20 in a secured or locked position.

When the base tooth 30 reaches the secured or locked position, the aperture finger 62 deflects inwardly to a locking position, and together with the aperture finger protrusion 66 and variable aperture stop wall 67 substantially surrounds and locks the positioning tooth 30 in the variable aperture 61, as best shown in FIG. 4. The aperture finger's 62 locking position may or may not be the same position as the initial aperture finger 62 equilibrium or static position that exists when the end cap 40 or 42 is first axially placed on the based section 15 or 25. The complementary and mechanical communication between the aperture finger protrusion 66, the tooth head 29, and the variable aperture stop wall 67 can comprise a second securing or locking mechanism 60, shown in FIGS. 2, 4 and 5.

In the locking position, shown in FIGS. 2 and 4-5, the aperture finger 62 and variable aperture stop wall 67 together provide a holding force or friction fit on the positioning tooth 30, translated to the positioning tooth 30 by the aperture finger protrusion 66 and variable aperture stop wall 67. The locking or holding force provided by the second securing or locking mechanism 60 will tend to minimize or retard rotational movement by the end cap 40 or 42 in an unlocking direction due to the obstruction provided by the aperture finger protrusion 66 against the base tooth head 29. The holding strength or force provided by the aperture finger 62 and variable aperture stop wall 67 may be augmented or controlled by selection and use of different materials with different resilient physical properties, or through the use of coating or adhesive substances between the aperture finger protrusion 66, variable aperture stop wall 67 and the positioning teeth 30. For example, a coating, such as silicone, or an adhesive such as epoxy, may be used to increase friction between the aperture finger protrusion 66, variable aperture stop wall 67 and the positioning teeth 30. Those of skill in the art will recognize that other substances or friction control mechanisms and material may be used to augment or control the holding force or strength and friction between the aperture finger protrusion 66, variable aperture stop wall 67 and the positioning teeth 30, such as roughened surfaces, dissimilar materials, and shape differences.

The positioning tooth 30 will remain in the locked position until sufficient force is applied to overcome the deflecting aperture finger's 62 holding force and permit removal of the end cap 40 or 42. In order to introduce such an unlocking force, the end cap 40 or 42 would be rotated in an opposite direction than was initially used to lock the end cap 40 or 42 onto the base section 15 or 25 as described above. In the embodiment shown in FIG. 2-4, the unlocking direction would be a counter clockwise direction. When the aperture finger 62 encounters a deflecting force sufficient to overcome its locking position and/or relative inertia at the locking position, the aperture finger 62 will again move or deflect in an outwardly direction Y shown in FIGS. 6-7. When such a removal force is introduced via opposite rotation of the end cap 40 or 42 relative to the base section 15 or 25, the first and second securing or locking mechanism 50 and 60 will be simultaneously or complementarily released or disengaged.

In the first securing or locking mechanism 50, as the end cap 40 or 42 is rotated away from the locked position, the aperture protrusions 431 and fixed aperture stop wall 47 in the narrow sections 439 will move and travel away from the base teeth 30 and its undercut sections 31. In this manner, the aperture protrusions 431 and undercut sections 31 will disengage. This will permit the base teeth 30 to move out of the narrow sections 439 and into the wide section 438 of the end cap's fixed apertures 45 thereby releasing the base teeth 30 from their locked positions. Simultaneously and complementarily, in the second securing or locking mechanism 60, the aperture finger 62 and aperture finger protrusion 66 will move and deflect outwardly and thereby permit the positioning tooth 30 to slideably travel away from the variable aperture stop wall 67, past the aperture finger protrusion 66 and out of aperture interior space 64 thereby releasing the base tooth 30 from its locked position. The end cap 40 or 42 can then be axially removed away from the implant base section 15 or 25.

FIGS. 2-7 show end caps 40 or 42 which have the same total number of end cap apertures 45 or 61 as corresponding base teeth 30. The disclosed embodiment includes six total aperture 45 and 61 and six corresponding base teeth or base extensions 30. If the locking apertures or passages 45 and 61 are to axially accept entry of extending base teeth 30, the end cap 40 must have at least the same number of locking apertures 45 and 61 as the number of extending base teeth 30. If there are two extending base teeth, then the there must be at least two locking apertures 45 or 61. If there are four extending base teeth 30, then there must be at least four locking apertures or passages 45 or 61 in order that the end cap 40 or 42 can be axially inserted and seated onto the implant base section 15 or 25. Those of skill in the art will recognize that other embodiments may include an end cap 40 or 42 having more apertures 45 or 61 than corresponding base teeth 30. These embodiments would then include one or more empty end cap apertures 45 and 61. Further, in other end cap aspects, the number of fixed apertures 45 could be the same as variable apertures 61, or the number of fixed apertures could be less than the number of variable apertures.

An additional advantageous aspect of the disclosed locking apertures or passages 45 and 61 is that they enable the end cap 40 or 42 to be selectively positioned or adjusted on the implant base section 15 or 25. For example, during preassembly of the implant body 20 and end cap 45 and/or 42. The end cap 40 or 42 can be adjustable relative to the implant body 20 and implant base section 15 or 25 about the longitudinal axis 5 of the implant body 20 to determine a selected axial delivery position or orientation. The number of locking apertures 45 and 61 determine the number of positions or rotational orientations at which the end cap 40 or 42 can be axially placed in or located on the implant base section 15 and 25. The greater the number of locking apertures 45 and 61 the larger the number of positions or rotational positions the end cap 40 can be adjusted and axially placed in or located on the implant base section 15 and 25. The more locking apertures or passages 45 and 61, the greater degree of choice and control a surgeon will have in selecting a rotational position for the end cap 40 to be axially placed in or located on the implant base section 15 and 25. This end cap aspect advantageously provides a surgeon selective control of where the end cap angulation θ and the end cap vertex height H will be positioned on the implant base section 15 or 25. The ability to selectively position the end cap angulation θ permits a surgeon to determine where the end cap angulation θ and end cap height H will be applied or imparted to an the adjacent vertebral body 100 or 105. Prior to insertion of the implant 10 into the intervertebral disc space 101, the surgeon can decide where the end cap angulation θ and the end cap vertex height H are desired or needed for a particular medical procedure or clinical application.

As noted previously, a surgeon can selectively position the end cap 40 on the implant base plate 15 or 25 by rotating the end cap 40 relative to the base section 15 or 25, either clockwise or counterclockwise, and then axially inserting the end cap locking apertures 45 and 61 onto the base teeth 30 at the desired or needed rotational position on the implant base plate 15. This aspect enables selective positioning or orientation of the end cap angulation θ which in turn permits the surgeon to decide where the end cap angulation 9 and end cap height H will be applied or imparted to an the adjacent vertebral body 100 or 105. The clockwise or counterclockwise rotation of the end cap 40 or 42 moves or adjusts the end cap's 40 angulation θ and the end cap vertex height H relative to the implant base section 15 so as to position the end cap angulation θ and vertex height H at a desired or required point on the implant base section 15 or 25. For example at anterior, antereolateral, posterior or lateral points about the vertebral member 100 or 105, or vertebral disk space 101. This is in turn will position the end cap angulation θ and vertex height H at a desired or required point relative to the adjacent intervetebral member 100 or 105 once the implant 10 is inserted and positioned within the intervertebral space 191. The end cap 40 will then be able to impart desired or required angulation 9, orientation and vertex height H on the adjacent vertebral body at selected or required points on the adjacent vertebral body 100 or 105 to correct or improve the angulation, orientation, alignment and stabilization of the spine or spinal anatomy.

As noted above, the end cap 40 may be rotated so as to contact and impart angulation θ at different location points about the periphery of the adjacent vertebral body 100 or 105. The number of locking aperture or passages 45 and 61 impact the incremental degree of control, through clockwise or counterclockwise end cap 40 rotation, that a surgeon will have in selecting the end cap angulation θ position between the implant 10 and the adjacent vertebral body 100 or 105. In the embodiment shown in FIGS. 2-7, the end cap 40 has six locking apertures 45 and 61 which are evenly or equidistantly space in the area between the exterior contact surface 48 and seating surface 41. The equidistant spacing results in the locking apertures 45 and 61 being located and spaced apart from each other at about sixty degrees (60°) around the end cap 40. In this embodiment then, the end cap 40 can be rotationally advanced, clockwise or counterclockwise, in single or multiple increments of sixty degrees (60°) in order to rotationally position or reposition the end cap angulation θ position between the implant 10 and the adjacent vertebral body 100 or 105.

A greater degree of control in rotationally and incrementally advancing the end cap 40, about the implant base section 15, may be obtained by increasing the number of locking apertures or passages 45 and 61. For example, if the end cap 40 were to have eight (8) locking apertures or passages 45 and 61 evenly or equidistantly spaced in the area between the contact surface 48 and seating surface 41. Then, equidistant circular spacing would result in the locking apertures or passages 45 and 61 being located and spaced apart from each other at forty-five degrees (45°) around the substantially circular area between the contact surface 48 and seating surface 41 of the end cap 40. In this case, the end cap 40 can be rotationally advanced, clockwise or counterclockwise, in single or multiple increments of forty-five degrees (45°) in order to position or reposition the end cap angulation θ position between the implant 10 and the adjacent vertebral body 100 or 105. The larger number of locking apertures or passages 45 provides a surgeon the ability to rotationally position or reposition the end cap 40 in smaller discrete increments. This greater degree of control provides the surgeon with more precise control on where the end cap angulation θ will be positioned between the implant 10 and the adjacent vertebral body 100 or 105. In this manner, the selected angulation θ and end cap vertex height H can be imparted to an adjacent vertebral member 100 or 105 to thereby impart or drive angular orientation and height adjustment of the adjacent vertebral member 100 or 105 for correction or improved alignment, angulation, orientation, and stabilization of the spine or spinal anatomy.

In one aspect, assembling the implant 10 includes initially determining the type of end cap 40 or 42 that is to be attached to the body 20. The end cap 40 or 42 may be selected based on the size of the intervertebral space 101 and the anatomy of the vertebral members 100 and 105. The appropriate or desired axial approach position of the end cap 40 or 42 is then selected by a surgeon so that the end cap 40 or 42 can be axially placed on the on the implant base plate 15 or 25.

The proper end cap 40 or 42 and desired axial approach are determined, and the end cap 40 or 42 is axially placed on the base section 15 or 25 of the implant body 20. The one or more end cap fixed apertures 45 are aligned with the one or more corresponding base teeth or base extensions 30 that axially extend outward from the base section support surface 16 of the implant body 20. The end cap 40 or 42 is axially moved towards the implant body 20 with the base teeth 30 to insert the base teeth 30 into the wide sections 438 of the fixed apertures 45. The end cap 40 or 42 is moved towards the implant body 20 until the end cap seating surface 41 contacts against the base section support surface 16 of the implant body 20.

Once the end cap 40 or 42 is axially mounted onto the one or more base teeth or base extensions 30 via the corresponding wide section 438 of the one or more end cap apertures 45, the end cap 40 or 42 is rotated relative to the implant body 20 base section 15 or 25. In the embodiment illustrated in FIGS. 2-5, the end cap 30 is rotated in a clockwise direction. This rotation moves the base teeth 30 into the narrow sections 439 of the end cap apertures 45. This movement causes the aperture protrusions 431, that extend into the end cap apertures 45, to be moved underneath the base teeth heads 29 and into the base teeth undercut sections 31. The end cap 40 or 42 may be rotated until the base teeth heads 29 contact against the fixed apertures stop walls 47 and/or just until the aperture protrusions 431 move underneath the heads 29 and into the undercut sections 31.

In one aspect, the base teeth or base extensions 30 on the implant body 20 and the end cap apertures 45 each have the complementary and cooperating size and shape. As a result, rotation of the end cap 40 or 42 causes each of the plurality of end cap fixed aperture 45 to be secured around a corresponding base tooth or base extension 30 in a similar manner. In other aspects, one or more of the base teeth or base extensions 30 and/or fixed end cap apertures 45 may have different shapes and/or sizes. This may cause differing amounts of contact between the various base teeth or base extensions 30 and end cap apertures 45, however, the base teeth 30 and corresponding end cap apertures 45 would have complementary and cooperating shapes and/or sizes such that they permit rotation of the end cap 40 or 42 so that each end cap apertures 45 can at least be partially secured to corresponding base teeth 30.

As the base teeth 30 and corresponding end cap fixed apertures 45 are being secured to each other when the end cap 40 or 42 is positioned on the base sections 15 or 25, the end cap variable aperture 61 simultaneously aligns and is axially placed on a corresponding implant base tooth 30. The position of the base tooth 30 is arranged such that the variable aperture 61 aligns with a corresponding base tooth 30 when end cap 40 or 42 is axially positioned on the base section support surface 16 of the implant body 20. When the end cap 40 or 42 is fully seated on the exterior surface 16 of the base section 15 or 25, the base tooth 30 is located in the first interior space 64. And, as described previously, base extensions 30 have also entered into and are now positioned in corresponding wide sections 438 of the one or more end cap fixed apertures 45. As the end cap 40 or 42 is rotated relative to the implant body 20 base section 15 or 25, the positioning tooth 30 travels inside the variable aperture 61 from the first interior space 64 towards the aperture finger protrusion 66 and the variable aperture stop wall 67 in the second interior space 65.

As the positioning tooth 30 continues to travel inside the variable aperture 61, the positioning tooth 30 encounters the aperture finger protrusion 66. The base tooth 30 will impart a deflecting force to outwardly deflect the aperture finger protrusion 66 and by extension the aperture finger 62. The deflection of aperture finger 62 the moves the obstructing aperture finger protrusion 66 which thereby permits the positioning tooth 30 to continue its travel further inside the variable aperture 61 from the first interior space 64 to towards the variable aperture stop wall 67 in the second interior space 65. When the positioning tooth 30 travels past the aperture finger protrusion 66, the aperture finger's 62 resilient or spring-like properties will force or bias the aperture finger 62 back an inward direction toward the base tooth 30.

Once the positioning tooth 30 travels past the aperture finger protrusion 66, as shown in FIG. 4, the positioning tooth 30 will reach and abut up against the variable aperture stop wall 67 which prevent further travel of the positioning tooth 30 inside the variable aperture 61. The aperture finger 62 will deflect back towards the base tooth and together with the aperture finger protrusion 66 and variable aperture stop wall 67 will substantially surround and lock the positioning tooth 30 in the variable aperture 61, as best shown in FIGS. 2 and 4. The plurality of base teeth 30 traveling in the other end cap fixed apertures 45 will simultaneously reach their corresponding fixed aperture stop walls 47 thereby also preventing further travel of the positioning teeth 30 in the other end cap fixed apertures 45. When at least one positioning or base tooth 30 reaches and abuts against a corresponding stop wall 47 or 67, the end cap 40 or 42 has reached the locking position on the implant base section 15 or 25, as best shown in FIGS. 2 and 4. At this point, the end cap 40 or 42 is attached and secured to the implant body 20 base section 15 or 25 in an engaged or locked position.

The implants 10 and end caps 40, 42 may be implanted within a living patient for the treatment of various spinal disorders. The implants 10 and end caps 40, 42 may also be implanted in a non-living situation, such as within a cadaver, model, and the like. The non-living situation may be for one or more of testing, training, and demonstration purposes.

The end caps disclosed in this disclosure are preferably comprised of biocompatible materials substrates which can be used in combination with implants or devices configured to be inserted into an intervertebral space and contact against adjacent vertebral members. The biocompatible material substrate may include, among others, polyetheretherketone (PEEK) polymer material, homopolymers, co-polymers and oligomers of polyhydroxy acids, polyesters, polyorthoesters, polyanhydrides, polydioxanone, polydioxanediones, polyesteramides, polyaminoacids, polyamides, polycarbonates, polylactide, polyglycolide, tyrosine-derived polycarbonate, polyanhydride, polyorthoester, polyphosphazene, polyethylene, polyester, polyvinyl alcohol, polyacrylonitrile, polyamide, polytetrafluorethylene, poly-paraphenylene terephthalamide, polyetherketoneketone (PEKK); polyaryletherketones (PAEK), cellulose, carbon fiber reinforced composite, and mixtures thereof. The biocompatible material substrate may also be a metallic material and may include, among others, stainless steel, titanium, nitinol, platinum, tungsten, silver, palladium, cobalt chrome alloys, shape memory nitinol and mixtures thereof. The biocompatible material used can depend on the patient's need and physician requirements.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

While embodiments of the invention have been illustrated and described in the present disclosure, the disclosure is to be considered as illustrative and not restrictive in character. The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant for insertion into an intervertebral space between a first and second vertebral member, the implant comprising:
    an implant body comprising a base section, the base section comprising at least a first base tooth and a second base tooth;
    an end cap adapted for selective axial positioning at a selected point on the base section, the end cap comprising
        an exterior contact surface that faces away from the implant body when the end cap is positioned on the base section,
        a seating surface adapted to contact the base section when the end cap is positioned on the implant body,
        an end cap angulation,
        a fixed aperture extending through the exterior contact surface and the seating surface adapted to receive a corresponding first base tooth, and
        a variable aperture extending through the exterior contact surface and the seating surface adapted to receive a corresponding second base tooth;
    wherein the fixed aperture and variable aperture are configured to complementarily engage corresponding first and second base teeth to securely maintain the end cap positioned on the base section; and
    wherein the implant imparts the end cap angulation to an adjacent vertebral body at the selected point when the implant is positioned in the intervertebral space.

2. The implant of claim 1, wherein the end cap is rotatable relative to the base section about an implant axis.

3. The implant of claim 1, wherein
    the first and second base teeth comprise a stem connected to an adjacent tooth head forming an undercut section;
    the fixed aperture comprises
        a wide section adapted to receive a corresponding tooth head, and
        a narrow section having an aperture projection adapted to engage the undercut section when the end cap is rotationally positioned on the base section; and
    the variable aperture comprises
        a first and second interior space adjacent to a flexible aperture finger having a finger protrusion that extends between the first and second interior spaces,
    wherein the first interior space is adapted to receive a corresponding base tooth and the aperture finger is adapted to deflect and permit the base tooth to enter the second interior space when the end cap is rotationally positioned on the base section;
    wherein the fixed and variable apertures and corresponding base teeth have complementary configurations that simultaneously provide a locking engagement when the end cap is positioned on the base section.

4. The implant of claim 1, wherein the end cap angulation comprises an angular value in the range of between zero degrees to fifteen degrees (0°-15°).

5. The implant of claim 1, wherein the end cap angulation is an angular value selected from the group consisting of 0°, 4°, 8° and 15°.

6. The implant of claim 1, wherein the end cap further comprises an end cap height measured relative to the seating surface which enables the implant to both impart end cap height and end cap angulation to the adjacent vertebral body at the selected point.

7. The implant of claim 3, wherein the locking engagement is an interference fit, a compression fit or a friction fit.

8. The implant of claim 1, wherein the fixed and variable apertures are spaced and located to enable complementary alignment with the base teeth to permit the end cap to be axially inserted onto the base section.

9. The implant of claim 8, wherein the base teeth are spaced and located equidistantly about the end cap.

10. The implant of claim 1, wherein the first base tooth has a height that is greater than a height of the fixed aperture and the second base tooth has a height that is greater than a height of the variable aperture.

11. The implant of claim 1, wherein the seating surface extends transverse to an axis defined by the fixed aperture and includes a ledge portion and the first base tooth includes an undercut section configured for disposal of the ledge portion to provide a locking engagement, the undercut including a planar end surface extending between planar top and bottom surfaces.

12. An end cap adapted for use with an implant having an implant body with at least one base section having a plurality of base extensions, the end cap comprising:
    an exterior contact surface;
    a seating surface;

a substantially vertical exterior cap wall extending between the exterior contact surface and the seating surface;

a fixed aperture extending through the exterior contact surface and the seating surface adapted to receive a corresponding first base extension, and a variable aperture extending through the exterior contact surface and the seating surface adapted to receive a corresponding second base extension;

wherein the fixed aperture and variable aperture are configured to complementarily engage corresponding first and second base extensions to securely maintain the end cap positioned on the base section;

wherein the fixed and variable apertures enable the end cap to be axially positioned at a selected point on the implant base section; and wherein the end cap positioned on the implant imparts an end cap angulation to an adjacent vertebral body at the selected point when the implant is axially placed and rotationally positioned in an intervertebral space.

13. The end cap of claim 12, wherein the end cap further comprises an end cap height measured relative to the seating surface which enables the end cap positioned on the implant to both impart end cap height and end cap angulation to the adjacent vertebral body at the selected point.

14. The end cap of claim 12, wherein the end cap is rotatable relative to the base section about an implant longitudinal axis so that the end cap angulation coincides to the selected point.

15. The end cap of claim 12, wherein the fixed aperture comprises
a wide section adapted to receive a corresponding tooth head, and
a narrow section having an aperture projection adapted to engage the undercut section when the end cap is rotationally positioned on the base section; and the variable aperture comprises
a first and second interior space adjacent to a flexible aperture finger having a finger protrusion, wherein the first interior space is adapted to receive a corresponding base extension and the aperture finger is adapted to deflect and permit the base extension to enter the second interior space when the end cap is rotationally positioned on the base section;

wherein the fixed and variable apertures and corresponding base extensions have complementary configurations that simultaneously provide a locking engagement when the end cap is positioned on the base section.

16. The end cap of claim 12, wherein the end cap angulation comprises an angular value in the range of between zero degrees to fifteen degrees (0°-15°).

17. The end cap of claim 12, wherein the first base extension has a height that is greater than a height of the fixed aperture such that a tip of the first base extension extends through a proximal surface of the fixed aperture when the first base extension is disposed in the fixed aperture and the second base extension has a height that is greater than a height of the variable aperture such that a tip of the second base extension extends through a proximal surface of the variable aperture when the second base extension is disposed in the variable aperture.

18. The end cap of claim 12, wherein the seating surface extends transverse to an axis defined by the fixed aperture and comprises a ledge portion and the first base extension includes an undercut section configured for disposal of the ledge portion to provide a locking engagement, the undercut including a planar end surface extending between planar top and bottom surfaces.

* * * * *